US012752089B2

(12) United States Patent
Thomas

(10) Patent No.: US 12,752,089 B2
(45) Date of Patent: Oct. 6, 2026

(54) COMPOSITE MEDICAL BALLOON WITH HYBRID OUTER LAYER AND RELATED PRODUCTION METHOD

(71) Applicant: C.R. BARD, INC., Franklin Lakes, NJ (US)

(72) Inventor: Kyle Andrew Thomas, Phoenix, AZ (US)

(73) Assignee: C.R. BARD, INC., Franklin Lakes, NJ (US)

( * ) Notice: Subject to any disclaimer, the term of this patent is extended or adjusted under 35 U.S.C. 154(b) by 582 days.

(21) Appl. No.: 18/017,739

(22) PCT Filed: Aug. 7, 2020

(86) PCT No.: PCT/US2020/045433
§ 371 (c)(1),
(2) Date: Jan. 24, 2023

(87) PCT Pub. No.: WO2022/031297
PCT Pub. Date: Feb. 10, 2022

(65) Prior Publication Data
US 2023/0264000 A1 Aug. 24, 2023

(51) Int. Cl.
*A61M 25/10* (2013.01)

(52) U.S. Cl.
CPC ...... *A61M 25/104* (2013.01); *A61M 25/1029* (2013.01); *A61M 2025/1075* (2013.01)

(58) Field of Classification Search
CPC .. A61M 2025/1075; A61M 2025/1084; A61M 25/005; A61M 25/0012; A61M 25/10; A61M 25/104; A61M 25/1029; A61M 25/1027
See application file for complete search history.

(56) References Cited

U.S. PATENT DOCUMENTS

| | | | | |
|---|---|---|---|---|
| 2004/0127850 | A1* | 7/2004 | Steadham | A61M 25/10 604/103 |
| 2007/0138694 | A1 | 6/2007 | Sridharan | |
| 2007/0213759 | A1* | 9/2007 | Osborne | A61M 25/10 606/192 |
| 2008/0033477 | A1* | 2/2008 | Campbell | A61M 25/1029 606/194 |
| 2008/0183132 | A1* | 7/2008 | Davies | A61M 25/1029 604/103.09 |

(Continued)

FOREIGN PATENT DOCUMENTS

| | | | |
|---|---|---|---|
| CN | 105579215 | A | 5/2016 |
| JP | 2020073176 | A | 5/2020 |
| WO | 2010051488 | A1 | 5/2010 |

(Continued)

*Primary Examiner* — Katherine H Schwiker
(74) *Attorney, Agent, or Firm* — Dickinson Wright PLLC; Andrew D. Dorisio; Nicholas P. Coleman

(57) ABSTRACT

A composite medical balloon includes a base balloon with first and second tapered portions (108) and a barrel portion (106) therebetween. The base balloon includes one or more fiber layers. A hybrid layer is applied over the base balloon, such as over the fiber layer. The hybrid layer includes a tube (70) for covering the barrel portion (106) and a spiral wrapping (80) for covering one or both of the first and second tapered portions (108). Related methods of forming of such a balloon are also disclosed.

18 Claims, 13 Drawing Sheets

(56) References Cited

U.S. PATENT DOCUMENTS

| | | | | |
|---|---|---|---|---|
| 2010/0243135 | A1 * | 9/2010 | Pepper | A61M 25/1029<br>156/189 |

FOREIGN PATENT DOCUMENTS

| | | | |
|---|---|---|---|
| WO | 2013134696 | A1 | 9/2013 |
| WO | 2014176422 | A1 | 10/2014 |
| WO | 2018183387 | A1 | 10/2018 |

* cited by examiner

COMPOSITE MEDICAL BALLOON WITH HYBRID OUTER LAYER AND RELATED PRODUCTION METHOD

BACKGROUND

Medical balloons are widely used in medical procedures. Typically, an uninflated medical balloon is inserted into a body space. When the medical balloon is inflated, the volume of the medical balloon expands, and the body space is similarly expanded.

In procedures such as angioplasty, the medical balloon may be used to open a collapsed or blocked artery. A typical medical balloon includes a central barrel portion between tapered or conical portions. The medical balloon may be provided in a non-compliant form by including one or more fiber layers, but compliant and semi-compliant forms are also known in the art.

To provide an outer layer for a medical balloon, past proposals have been made for cutting the ends of a tubular film longitudinally to form radially divided segments that may overlap to surround the tapered end more precisely when attached thereto. However, this leads to the creation of a number of longitudinal seams, which may be undesirable for some applications. Furthermore, if not done with great care, the results from forming the seams can be inconsistent, can lead to longitudinally extending fins. The manufacturing process involving the cutting of an outer layer preform can be complicated and costly, typically requiring an entirely manual process.

Accordingly, a need is identified for a medical balloon that overcomes any or all of the foregoing limitations and possibly others that have yet to be identified.

SUMMARY

An object of the disclosure is to provide a composite medical balloon including a hybrid layer including a tube for covering a barrel portion and a spiral wrapping for covering one or both of the tapered or cone portions.

According to a first aspect of the disclosure, a composite medical balloon comprises a base balloon layer including first and second tapered portions with a barrel portion therebetween. A hybrid layer includes a tube for covering the barrel portion and a spiral wrapping for covering at least one of the first and second tapered portions.

In one embodiment, the tube comprises an extruded or blow-molded material, which is substantially equal in length to the barrel portion of the base balloon layer. The tube may comprise a polyamide, and the base balloon layer may also comprise a polyamide. The spiral wrapping may comprise a spirally wound ribbon of material extending from a proximal end of the at least one tapered portion to a distal end of the at least one tapered portion. The spiral wrapping may overlap with the tube at a transition from the at least one tapered portion to the barrel portion. The spiral wrapping may comprise a polyether block amide, such as PEBAX, and may cover both tapered portions of the base balloon layer. The balloon may further include a fiber layer over the base balloon layer.

According to a further aspect of the disclosure, a composite medical balloon is provided. The composite medical balloon comprises balloon including first and second tapered portions having a barrel portion therebetween. A hybrid layer is adhesively attached to the balloon. The hybrid layer comprises a tube for covering the barrel portion, a first spirally wrapped ribbon of material for covering the first tapered portion, and a second spirally wrapped ribbon of material for covering the second tapered portion.

In one embodiment, the first spirally wrapped ribbon of material includes a plurality of overlapping winds, including one wind overlapping an edge of the tube that is adhesively bonded at the overlap. The tube and the balloon may each comprise the same material, such as a polyamide (Nylon). The first and second spirally wrapped ribbons of material comprise a polyether block amide (PEBAX). The tube may be substantially equal in length to a length of the barrel portion of the base balloon layer. The balloon may also include a fiber layer.

A further aspect of the disclosure pertains to a method of forming a composite medical balloon. The method comprises providing a balloon having a barrel portion between first and second tapered portions. The method further comprises forming a hybrid layer on the balloon by applying a tube over the barrel portion of the balloon, and applying a spiral wrapping along one or both of the first and second tapered portions.

In one embodiment, the method includes a step of providing an adhesive to the balloon prior to the forming step. The method may further include the step of inflating the balloon prior to the step of providing an adhesive, deflating the balloon prior to the step of applying the tube, and re-inflating the balloon prior to the step of applying the spiral wrapping. The step of applying the spiral wrapping may comprise applying a spirally wrapped ribbon of material to each of the first and second tapered portions of the balloon. The method may further include the step of laminating the balloon, the tube, and the spiral wrapping.

BRIEF DESCRIPTION OF THE DRAWINGS

The above and further advantages of the disclosure may be better understood by referring to the following description in conjunction with the accompanying drawings in which:

FIGS. 14, 15, 16, 17, 17A, and 18 illustrates a manner of providing a fiber-reinforced medical balloon with a hybrid outer layer.

Figure 1:
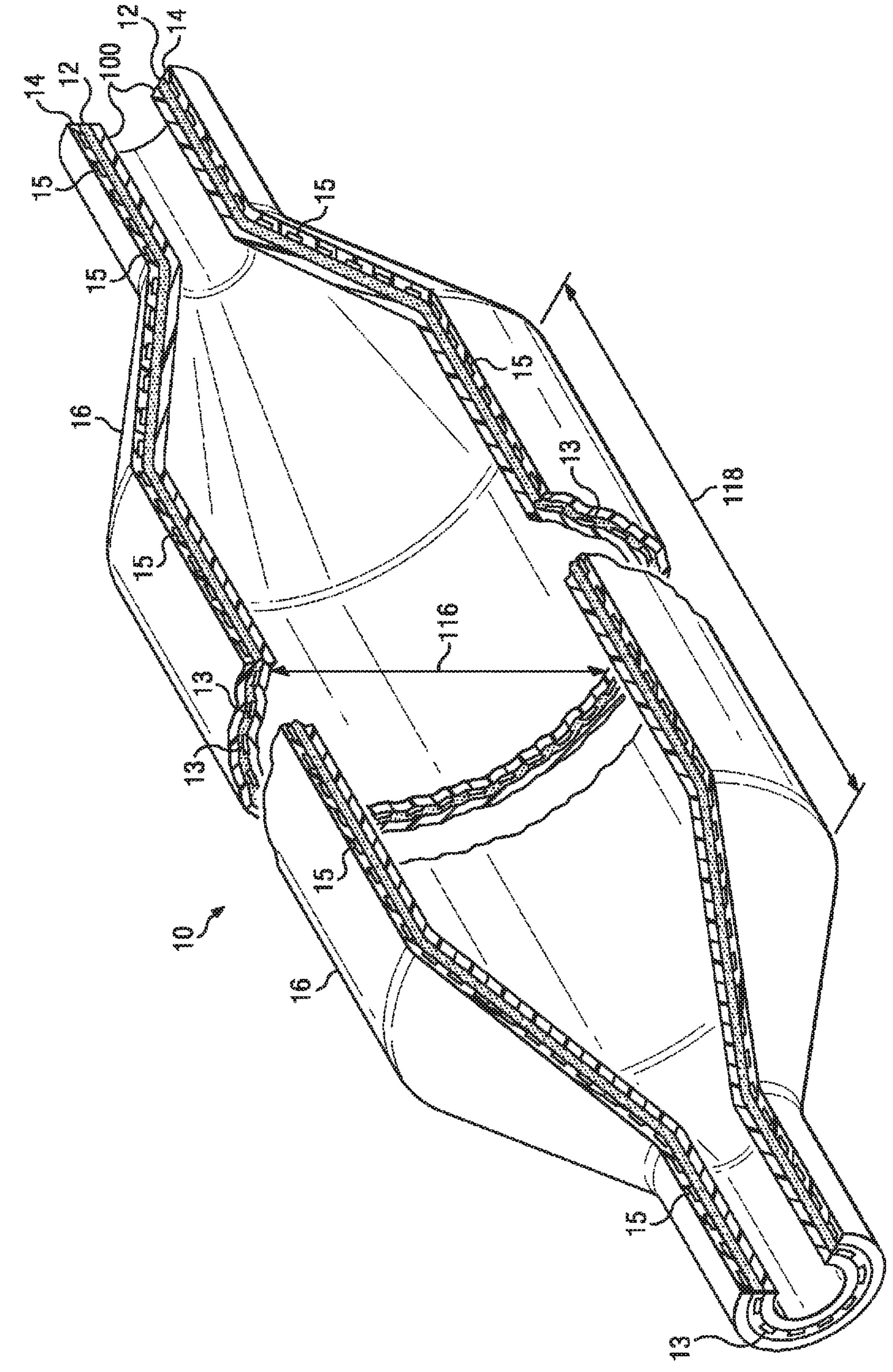
FIG. 1 illustrates a semi-cross section of a medical balloon.

The dimensions of some of the elements may be exaggerated relative to other elements for clarity or several physical components may be included in one functional block or element. Further, sometimes reference numerals may be repeated among the drawings to indicate corresponding or analogous elements. Moreover, some of the items depicted in the drawings may be combined into a single function.

DETAILED DESCRIPTION

In the following detailed description, numerous specific details are set forth to provide a thorough understanding of the present invention. The disclosed embodiments may be practiced without these specific details. In other instances, well-known methods, procedures, components, or structures may not have been described in detail so as not to obscure the present invention.

The principles and operation of systems and methods of the disclosure may be better understood with reference to the drawings and accompanying descriptions. The invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

Certain features of the invention that are, for clarity, described in the context of separate embodiments, may also be provided in combination in a single embodiment. Conversely, various features of the invention that are, for brevity, described in the context of a single embodiment, may also be provided separately or in any suitable sub-combination.

With reference to FIG. 1, a partial cross section of an inflated composite medical balloon 10 is shown. In the illustrated embodiment, and as discussed further in the following description, the balloon 10 may optionally be fiber-reinforced and, as a result, is substantially non-compliant, having limited expansion characteristics. Because the medical balloon 10 is non-compliant, once fully inflated, a diameter 116 of it does not substantially change as the interior pressure increases. As noted further below, the use of a fiber layer is considered entirely optional.

The diameter 116 of an inflated fiber-reinforced medical balloon 10 in accordance with the one embodiment may be about ten millimeters, but may vary depending on the application. The length of an inflated fiber-reinforced medical balloon 10 in accordance with one embodiment may be about eight centimeters. A balloon 10 with a length 118 of 2-200 centimeters or more is possible. The inclination angle of a tapered or cone portion 108 of an inflated fiber-reinforced medical balloon 10 in accordance with the disclosed embodiment may be about twenty degrees. It will be recognized by those having skill in the art that the fiber-reinforced balloon 10 could be made in a wide variety of diameters 116 and lengths and with a variety of inclinations at the tapered or cone portion 108 of the balloon 10, without limitation.

The fiber-reinforced medical balloon 10 may include a base layer 100 formed of a thin polymer material and a first layer 12 of thin inelastic fibers 13. The balloon 10 may include a second layer 14 made up of one or more fibers 15. An outer layer 16 over the fiber layer(s) 12, 14 may be included, as outlined in the following description.

Each fiber 13 is typically fixed relative to other fibers in the first fiber layer 12 and other fibers in the balloon 10. The thin inelastic fibers 13 of the first fiber layer 12 may be characterized by a high tensile strength, which provide superior burst strength. The fiber-reinforced balloon 10 may also resist abrasion, cuts, and punctures. It may be recognized that enhanced structural integrity may result from the fiber reinforcement.

Figure 2:
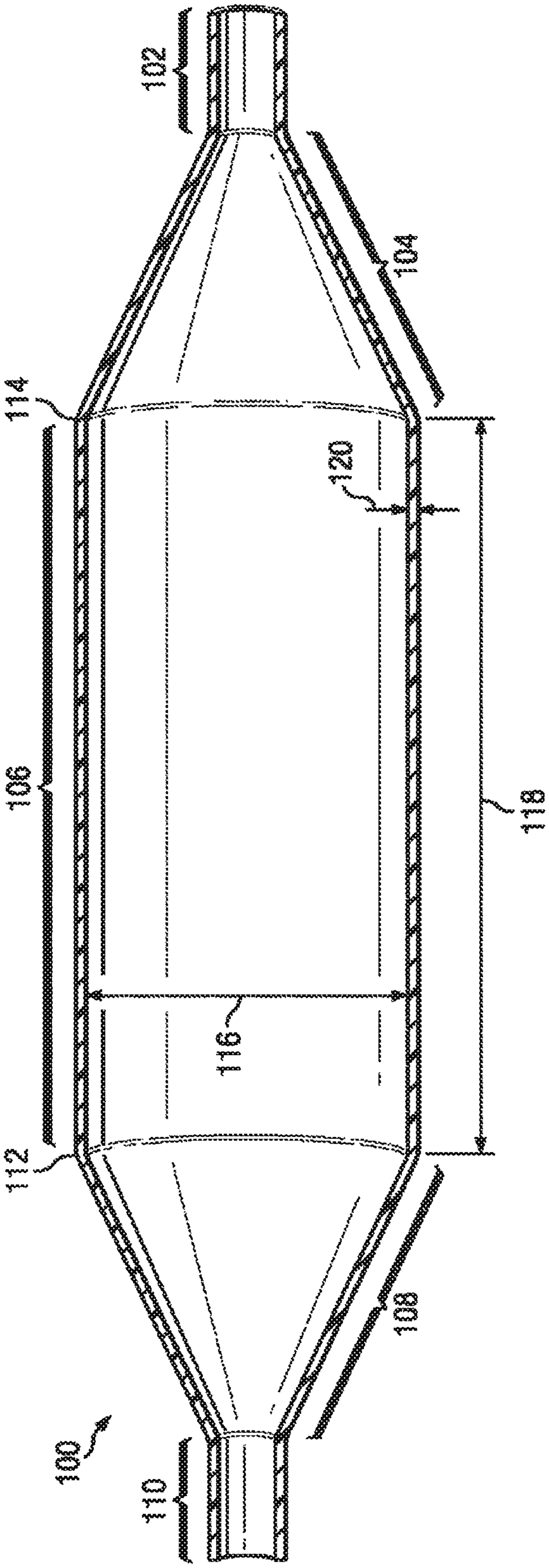
FIG. 2 illustrates an inflated balloon base layer.

With further reference to FIG. 2, the base layer 100 may be in the shape of a standard medical balloon, or any other suitable shape. The base layer 100 typically includes a first neck portion 102 that may be formed as a narrow cylinder fashioned to attach to a catheter shaft (see FIGS. 19, 20 and 21). A second neck portion 110 may be similarly formed as a narrow tube. The first neck portion 102 is formed adjacent to a first cone or tapered portion 104. The first cone portion 104 expands to meet a barrel portion 106 having a working length 118, marked by a first transition 114. The first cone portion 104 is typically constructed at an angle of about twelve to twenty degrees. The central region or barrel portion 106 meets the second cone or tapered portion 108 at a second transition 112. The second cone portion 108 meets the second neck portion 110.

The base layer 100 is typically formed of a thin film polymeric material, or other suitable materials with high strength relative to film thickness. Polymers and copolymers that can be used for the base layer 100 include the conventional polymers and copolymers used in medical balloon construction, such as, but not limited to, polyethylene, (PET), polycaprolactam, polyesters, polyethers, polyamides, polyurethanes, polyimides, ABS, nylons, copolymers, polyester/polyether block copolymers, ionomer resins, liquid crystal polymers, and rigid rod polymers. The base layer 100 may typically be formed as a blow-molded balloon of a polymer material, such as for example a polyamide, such as nylon.

Figure 3:
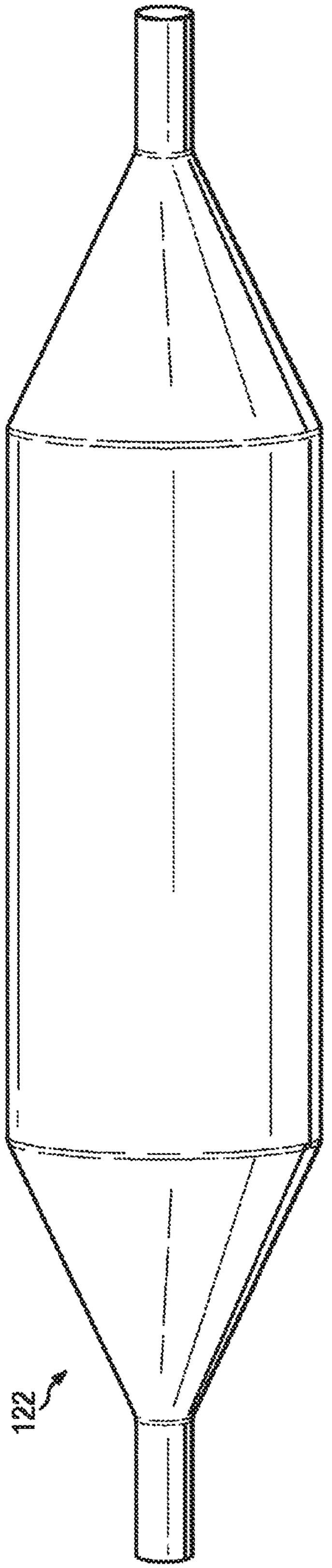
FIG. 3 illustrates a balloon-shaped mandrel.

The base layer 100 may comprise a polymer, which has been cured into the shape of a balloon, may be formed. This base layer 100 of a cured polymer may form the inner polymeric wall of the fiber reinforced balloon. With reference to FIG. 3, a removable mandrel 122 may be used as a base for application of the polymer coating. After the polymer is cured, the mandrel 122 may be removed, such as by physical withdrawal, heat, or other known forms of dissolution.

A removable balloon similar to base layer 100 may be used as the mandrel 122. The mandrel 122 may be made from a variety of materials. The mandrel 122 may be made in the shape of the interior wall of the desired finished balloon. The mandrel 122 may be made of collapsible metal or polymeric bladder, foams, waxes, low-melting metal alloys, and the like. Once the composite balloon is developed and laminated, the mandrel 122 (i.e., base layer 100) may be removed by melting, dissolving, fracturing, compressing, pressurizing, or other suitable removal techniques.

Figure 4:
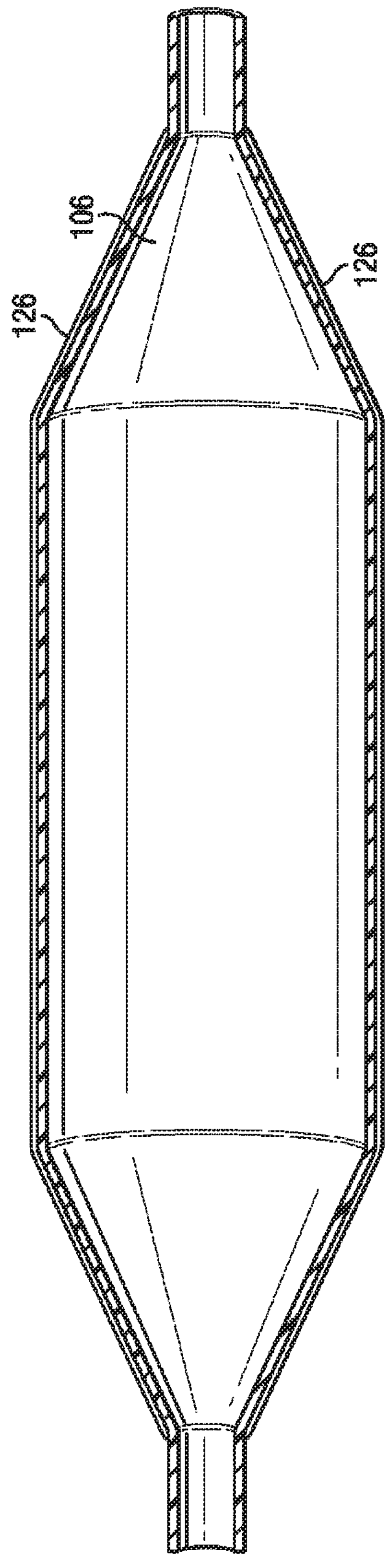
FIG. 4 illustrates a balloon base layer having an adhesive layer.

With reference to FIG. 4, it can be understood that a thin coating of an adhesive 126 is applied to the inflated base layer 100 or to the polymer-coated mandrel 122 prior to applying the first layer inelastic fibers 12. The adhesive 126 binds the fibers 13 sufficiently to hold them in position when the fibers 13 are placed on the base layer 100. In accordance with one embodiment, a very thin coat of adhesive 126 is applied to the base layer 100, such as for example 1-MP adhesive, which is a known solution of a polyurethane based polymer and methyl ethyl ketone and methylene chloride, but other forms of adhesive could be used.

Figure 5:
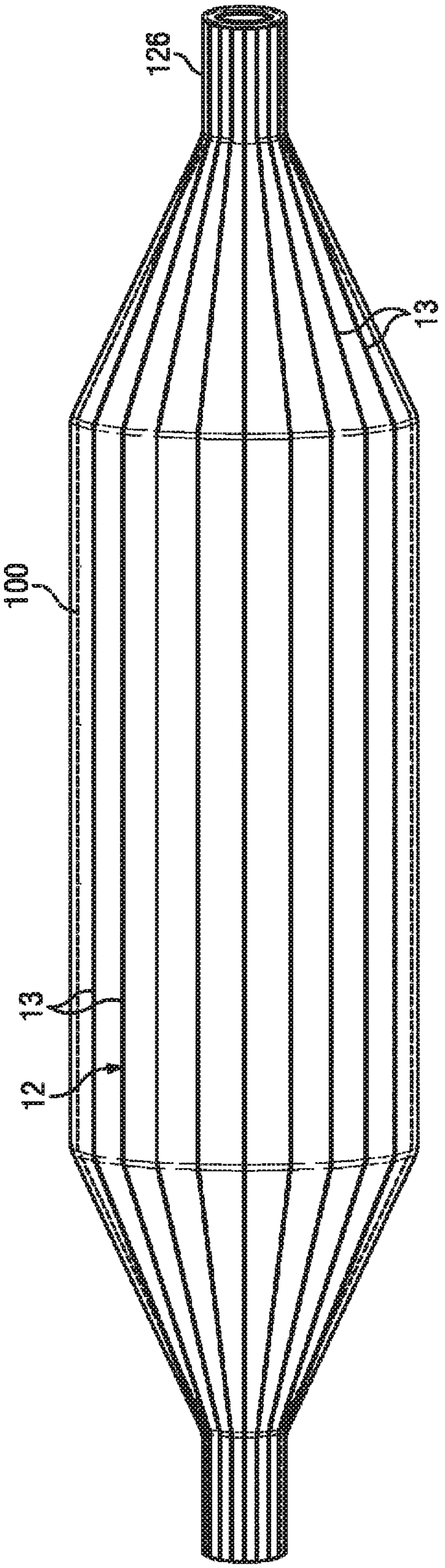
FIG. 5 illustrates a first fiber layer.
Figure 6:
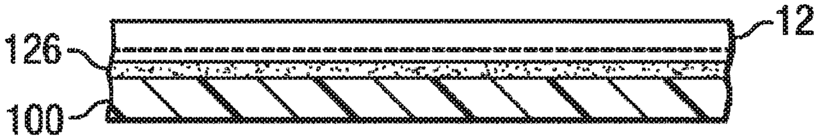
FIG. 6 illustrates a cross-section of a balloon base layer, adhesive layer and first fiber layer.

One or more fibers 13 are applied to the base layer 100 to form a first fiber layer 12, as shown in FIGS. 5 and 6, which may be referred to as the "primary wind." The fibers 13 of the first fiber layer 12 may be inelastic fiber, typically made of an inelastic fibrous material. An inelastic fiber is a fiber that has very minimal elasticity or stretch over a given range of pressures. Some fibrous materials are generally classified as inelastic although the all fibrous material may have a detectable, but minimal, elasticity or stretch at a given pressure. The fibers 13 of the first fiber layer 12 may be high-strength fibers, typically made of a high-strength fibrous material. Some high strength inelastic fibrous materials may include Kevlar, Vectran, Spectra, Dacron, Dyneema, Terlon (PBT), Zylon (PBO), Polyimide (PIM), other ultrahigh molecular weight polyethylene, aramids, and the like.

In a disclosed embodiment, the fibers 13 of the first fiber layer 12 are ribbon-shaped, where the width of the fiber is larger than the thickness of the fiber. The fibers 13 may be flat so that the fiber has a rectangular cross-section. The fibers 13 used in the initial layer of fibers 12 may all be fibers 13 made of the same material and the same shape. Fibers 13 made from different materials may be used in the initial fiber layer 12. Fibers 13 made in different shapes may be used in the initial fiber layer 12. Ultrahigh Molecular Weight (UHMW) Polyethylene fiber 13, which has been flattened on a roll mill may be used to form the first fiber layer 12. To the flattened fiber 13 is applied an adhesive, such as the 1-MP adhesive. The fibers 13 may be arranged as 30 longitudinal fibers, each substantially equal in length to the length of the balloon 10.

The fibers 13 of the initial fiber layer 12 may be arranged so that each fiber 13 is substantially parallel to the long axis of the balloon 10. The density of the fibers 13 in the initial fiber layer 12 is determined by the number of fibers 13 or fiber winds per inch and the thickness of the fibers 13. In a disclosed embodiment of the first fiber layer 12 having longitudinally-placed fibers 13, a fiber density of generally about 15 to 30 fibers 13 having a fiber thickness of about 0.0005 to 0.001 inch and placed equidistant from one another provide adequate strength for a standard-sized fiber-reinforced medical balloon 10. Each of the fibers 13 is substantially equal in length to the balloon 10. The first fiber layer 12 may prevent longitudinal extension of the completed fiber-reinforced balloon 10.

Figure 7:
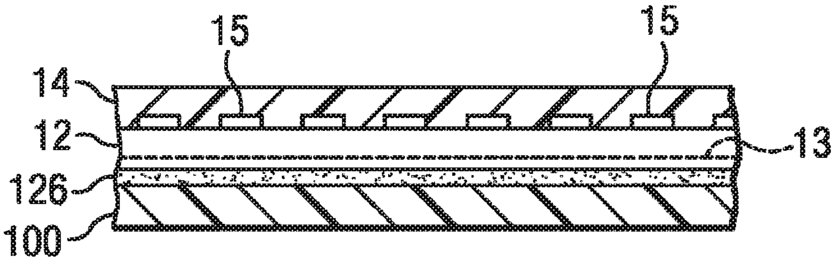
FIG. 7 illustrates a cross-section of a balloon base layer, adhesive layer and fiber layers.

In accordance with a disclosed embodiment, a second fiber layer 14 made with one or more high-strength inelastic fibers 15 is positioned along circumference of the balloon 10, as shown in FIG. 7. The circumferentially placed fibers 15 may be transverse or substantially transverse to the longitudinal axis of the balloon 10. The circumferential fibers 15 may prevent or minimize distension of the balloon diameter 116 at pressures between the minimal inflation pressure and the balloon burst pressure.

The fibers 15 of the second fiber layer 14 may be inelastic fiber, typically made of an inelastic fibrous material. An inelastic fiber is a member of a group of fibers that have very minimal elasticity or stretch in a given range of pressures. Some fibrous materials are generally classified as inelastic although the all fibrous material may have a detectable, but minimal elasticity or stretch at a given pressure. The fibers 15 of the second fiber layer 14 may be high-strength fibers, typically made of a high-strength fibrous material. Some high strength inelastic fibrous materials may include Kevlar, Vectran, Spectra, Dacron, Dyneema, Terlon (PBT), Zylon (PBO), Polyimide (PIM), other ultra-high molecular weight polyethylene, aramids, and the like.

In a disclosed embodiment, the fibers 15 of the second fiber layer 14 are ribbon-shaped, where the width of the fiber is larger than the thickness of the fiber. The fibers 15 may be flat so that the fiber has a rectangular cross-section. The fibers 15 used in the second layer of fibers 14 may all be fibers 15 made of the same material and the same shape. Fibers 15 made from different materials may be used in the second fiber layer 14. Fibers 15 made in different shapes may be used in the second fiber layer 14. UHMW polyethylene fiber 15, which has been flattened on a roll mill may be used to form the second fiber layer 14. To the flattened fiber 15 is applied a thin coat of an adhesive, such as the 1-MP adhesive. The fibers 15 may be arranged as a second fiber layer 14 may have a fiber density of 54 wraps per inch.

The fibers 15 of the second fiber layer 14 may be perpendicular to or substantially perpendicular to the fibers 13 placed longitudinally to form the first fiber layer 12. This transverse placement of the first fiber layer 12 and the second fiber layer 14 allows for maximum radial stability of the fiber-reinforced balloon 10. The placement of the fiber layers 12 and 14 distributes the force on the balloon surface equally, creating pixelized pressure points of generally equal shape, size, and density.

The fibers 13 of the first fiber layer 12 may be the same as or different from the fiber 15 of the second fiber layer 14. Specifically, the fibers 15 of the second fiber layer 14 may be made of a different material or materials than the fibers 13 of the first layer 12. The fibers 15 of the second layer 14 may be shaped differently from the fibers 13 of the first fiber layer 12. The characteristics of the fibers or combination of fibers used for the first or second fiber layers may be determined from the specific properties required from the resulting fiber-reinforced balloon 10.

With respect to the fiber density of the second fiber layer 14, in accordance with the disclosed embodiment, fiber 15 having a thickness of about 0.0005 to 0.001 inch and arranged in parallel lines with about 50 to 80 wraps per inch provides generally adequate strength. A single fiber 15 may form the second fiber layer 14, with the fiber 15 wound in a generally parallel series of circumferential continuous loops.

Figure 8:
FIG. 8 illustrates a cross-section of a balloon base layer, an adhesive layer, a first fiber layer, a second fiber layer, an outer coating layer and a final layer.

With reference to FIG. 8, a cross section of the integral layers of a fiber-reinforced medical balloon 10 is shown. The first fiber layer 12 and the second fiber layer 14 may be coated with an outer layer 16. The outer layer 16 may be, in the disclosed embodiment, a hybrid outer layer, as outlined further in the following description. A composite structure typically including a base layer 100, an adhesive 126, a first fiber layer 12, a second fiber layer 14 and an outer layer 16 forming a composite, non-compliant fiber-reinforced balloon 10 particularly suitable for medical uses. Typically, the fibers 13 and 15 are fixed when the fiber-reinforced balloon 10 is initially deflated, and then subsequently inflated and deflated during use.

Figure 9:
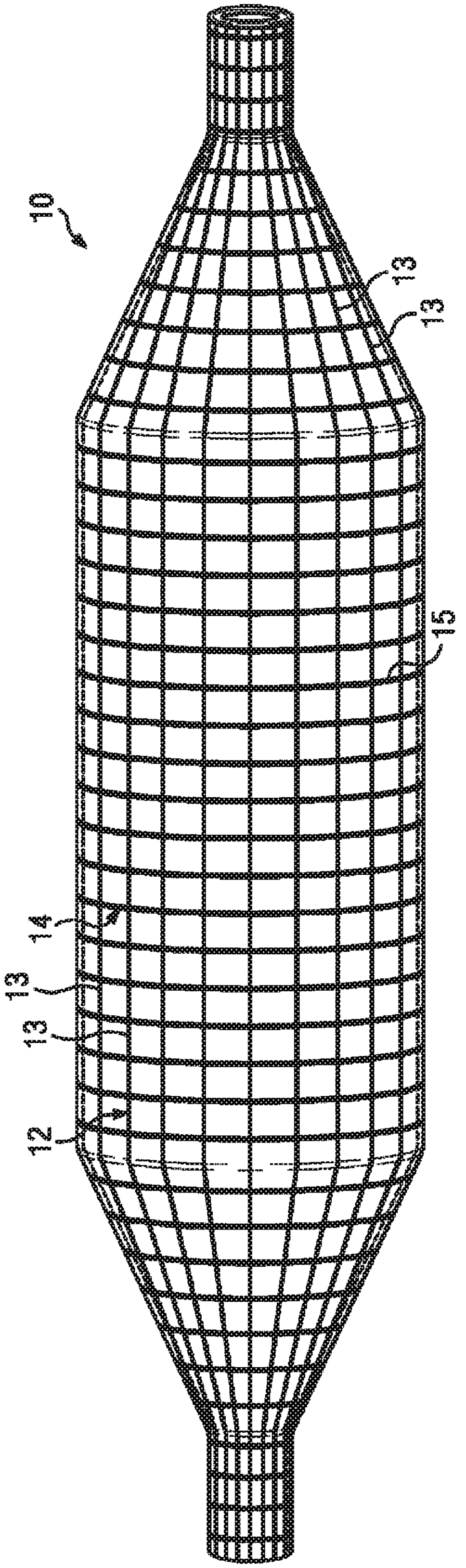
FIG. 9 illustrates a fiber-reinforced medical balloon with a longitudinal first fiber layer and a circumferential second fiber layer.

With reference to FIG. 9, a fiber reinforced balloon 10 in accordance with the disclosed embodiment, is shown. In this embodiment, the fibers 13 are parallel to the balloon 10 long axis.

Figure 10:
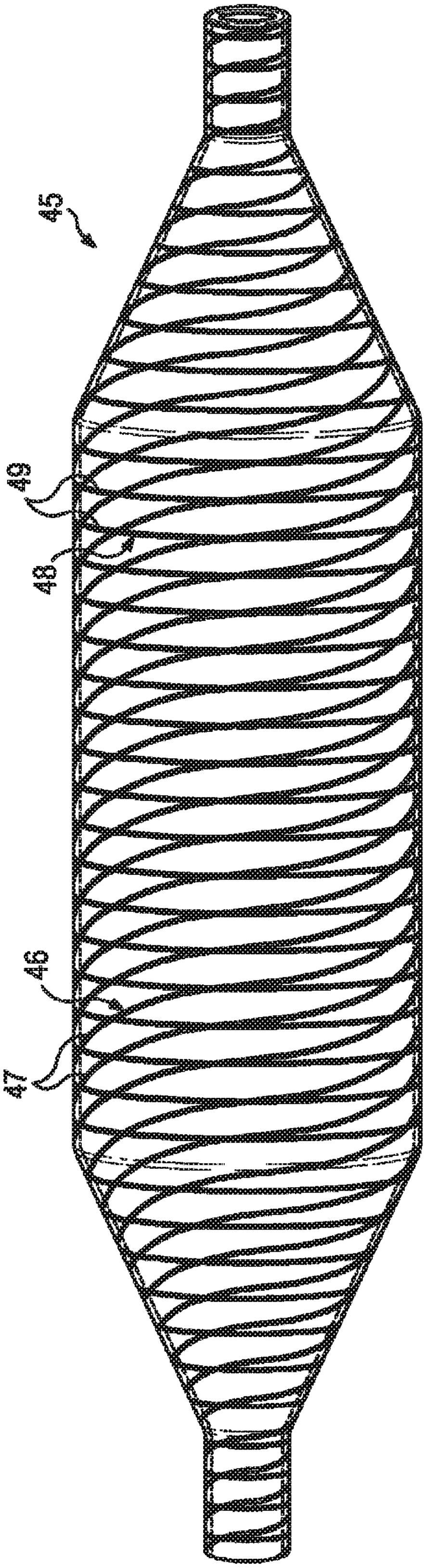
FIG. 10 illustrates a fiber-reinforced medical balloon with a first angled fiber layer and a second longitudinal second fiber layer.

With reference to FIG. 10, a fiber reinforced balloon 45, in accordance with another embodiment is shown. The fiber-reinforced balloon 45 may include a first fiber layer 46 with fibers 47 that lie at an angle to the longitudinal axis of the balloon 45. In this embodiment, neither the fibers 47 of the first fiber layer 46 nor the fibers 49 of the second fiber layer 48 are positioned parallel to the longitudinal axis of the balloon 45. In accordance with one embodiment, the fibers 47 of the first fiber layer 46 may be positioned parallel to a line at a five-degree angle to a line parallel to the longitudinal axis of the balloon 10. In accordance with another embodiment, the fibers 47 of the first fiber layer 46 may be positioned parallel to a line at a twenty-degree angle to a line parallel to the longitudinal axis of the balloon 10.

In accordance with another embodiment, the fibers 47 of the first fiber layer 46 may be positioned parallel to a line at a thirty-degree angle to a line parallel to the longitudinal axis of the balloon 10. In accordance with another embodiment, the fibers 47 of the first fiber layer 46 may be positioned parallel to a line at a forty-five-degree angle to a line parallel to the longitudinal axis of the balloon 10. It will be apparent to those having skill in the art that the fibers 47 may be placed at any appropriate angle.

Figure 11:
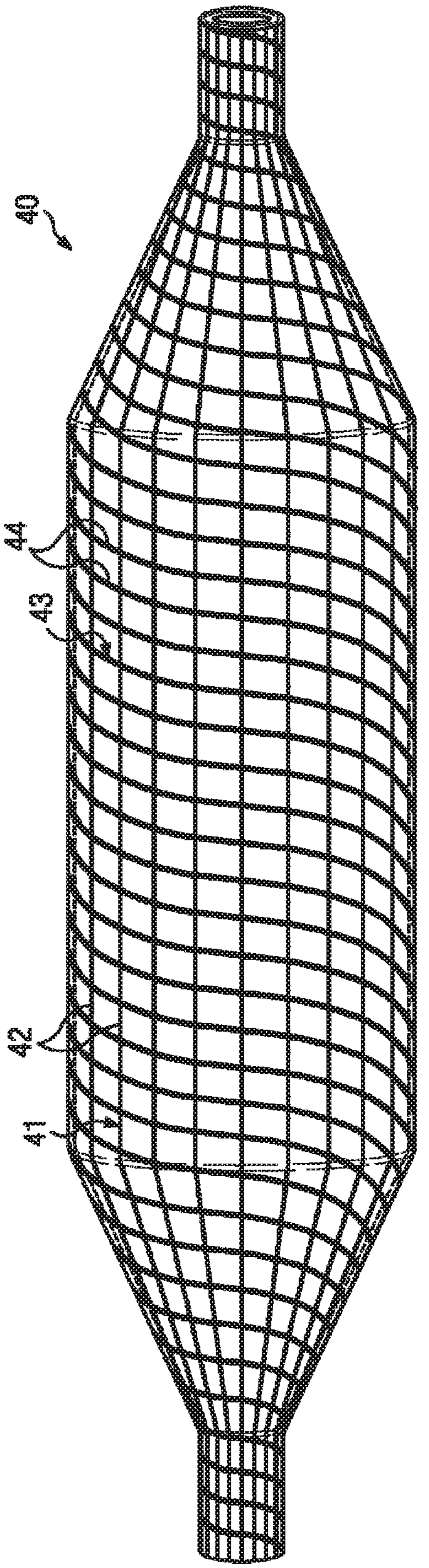
FIG. 11 illustrates a fiber-reinforced medical balloon having a first longitudinal fiber layer and a second angled fiber layer.

The fibers 49 of the second fiber layer 48 lie parallel to the circumference of the balloon 10. With reference to FIG. 11, a fiber-reinforced balloon 40 in accordance with another embodiment is shown. The fiber reinforced balloon 40 may include a second fiber layer 43 with fibers 44 that lie at an angle to the circumference of the balloon 40. In accordance with one embodiment, the fibers 44 of the second fiber layer 43 may be positioned parallel to a line at a five-degree angle to a line parallel to the circumference of the balloon 10.

The fiber 44 of the second fiber layer 43 may be positioned parallel to a line at a twenty-degree angle to a line parallel to the circumference of the balloon 10. In accordance with one embodiment, the fiber 44 of the second fiber layer 43 may be positioned parallel to a line at a thirty-degree angle to a line parallel to the circumference of the balloon 10. In accordance with one embodiment, the fiber 44 of the second fiber layer 43 may be positioned parallel to a line at a forty-five-degree angle to a line parallel to the circumference of the balloon 10. It will be apparent to those skilled in the art that the fibers 44 may be placed at any appropriate angle.

Figure 12:
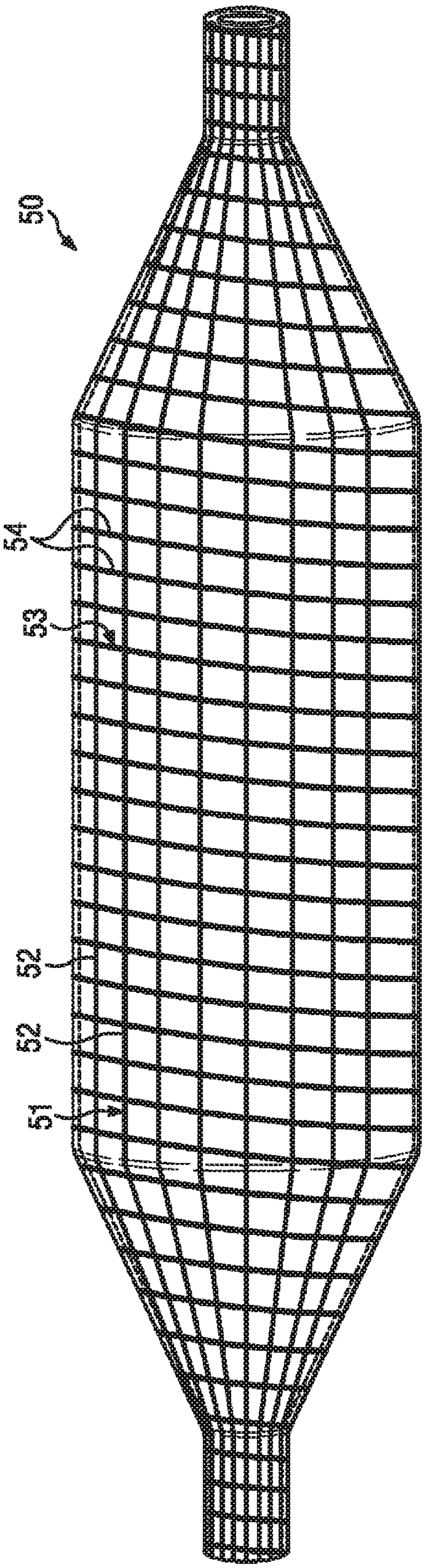
FIG. 12 illustrates a fiber-reinforced medical balloon having a longitudinal first fiber layer and an angled second fiber layer.

The fibers 42 of the first fiber layer 41 and the fibers 44 of the second fiber layer 43 are positioned perpendicularly relative to each other. With reference to FIG. 12, a fiber-reinforced balloon 50 in accordance with another embodiment is shown. A fiber-reinforced balloon 50 may include fibers 52 of the first fiber layer 51 and fibers 54 of the second fiber layer 53 positioned relatively at an angle other than a right angle.

Figure 13:
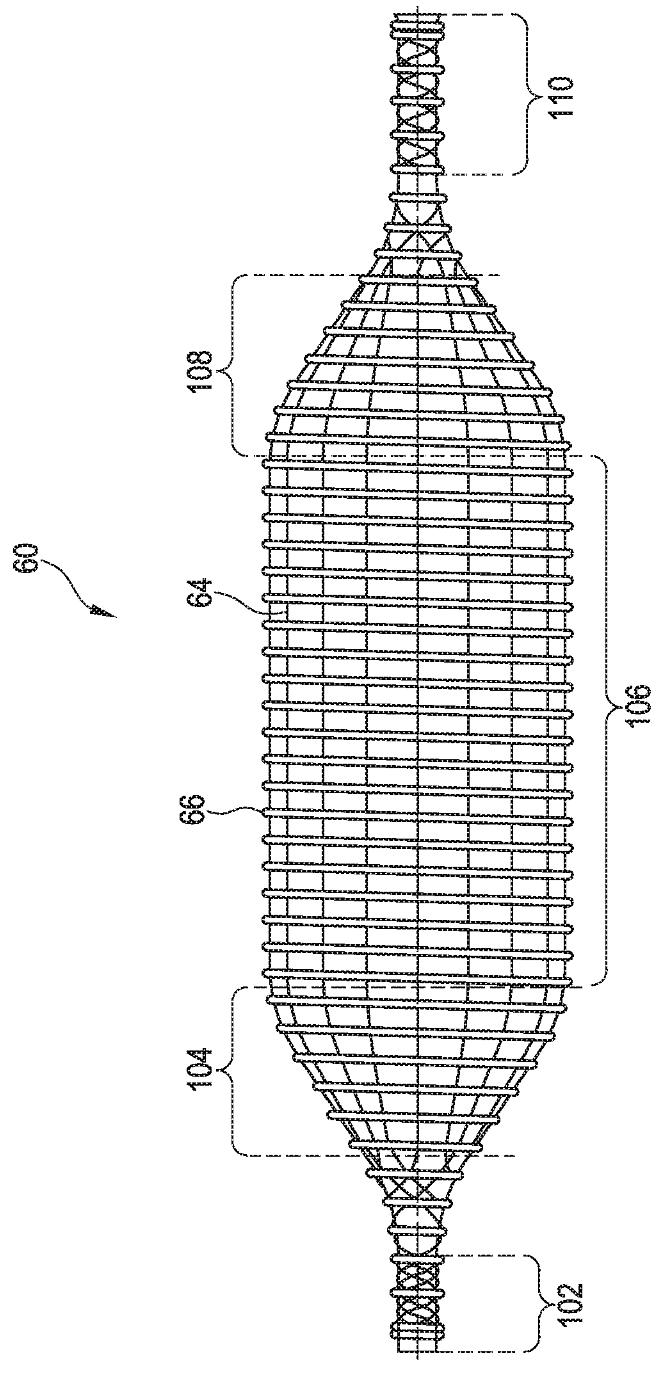
FIG. 13 illustrates an alternative embodiment of a fiber-reinforced medical balloon.

Referring to FIG. 13, a medical balloon 60 may also include a single continuous fiber forming a longitudinal fiber strand 64 and a hoop fiber strand 66. Specifically, the fiber 62 may be wrapped circumferentially around one end portion, such as neck portion 102, and directed longitudinally to the other end portion, or neck portion 110 (possibly at a non-zero angle to the longitudinal axis). The fiber 62 is then wrapped around the other end portion 110, and returned in the opposite longitudinal direction (again, possibly at a non-zero angle). The single continuous fiber 62 can continue to be wound back and forth along the balloon 60 for a desired number of longitudinal passes, and then would circumferentially or helically around the balloon 60 at a desired fiber pitch. A more complete description of the application to a single continuous fiber to a medical balloon 60 may be found in U.S. Pat. No. 10,485,949.

Figure 14:
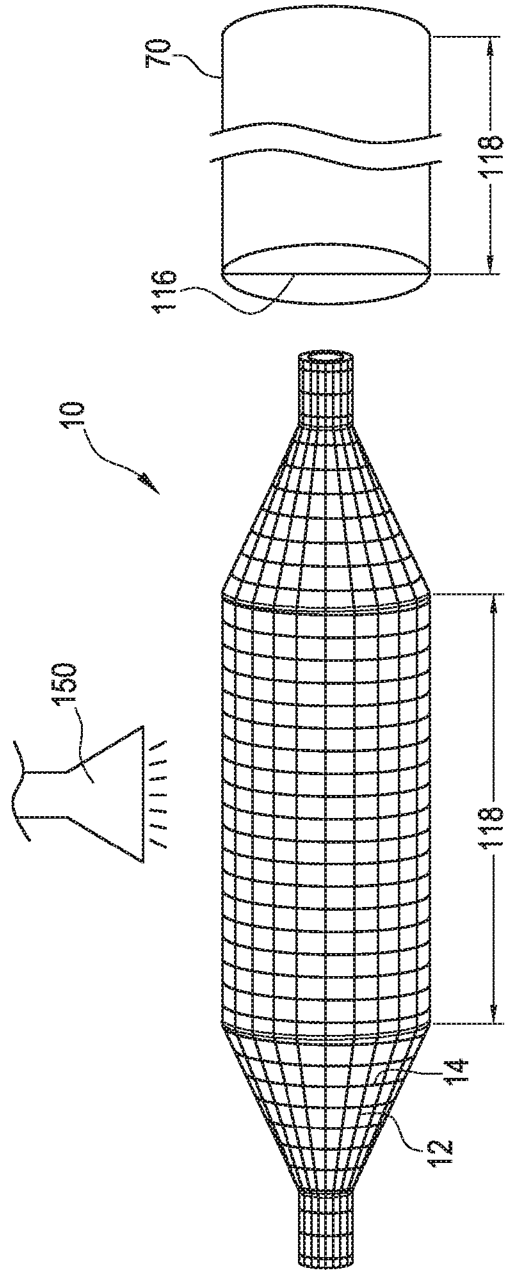
FIG. 14 illustrates an alternative embodiment of a fiber-reinforced medical balloon.
Figure 15:
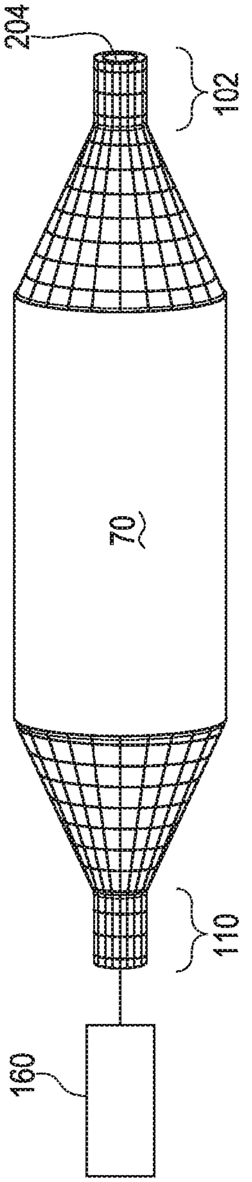
Figure 16:
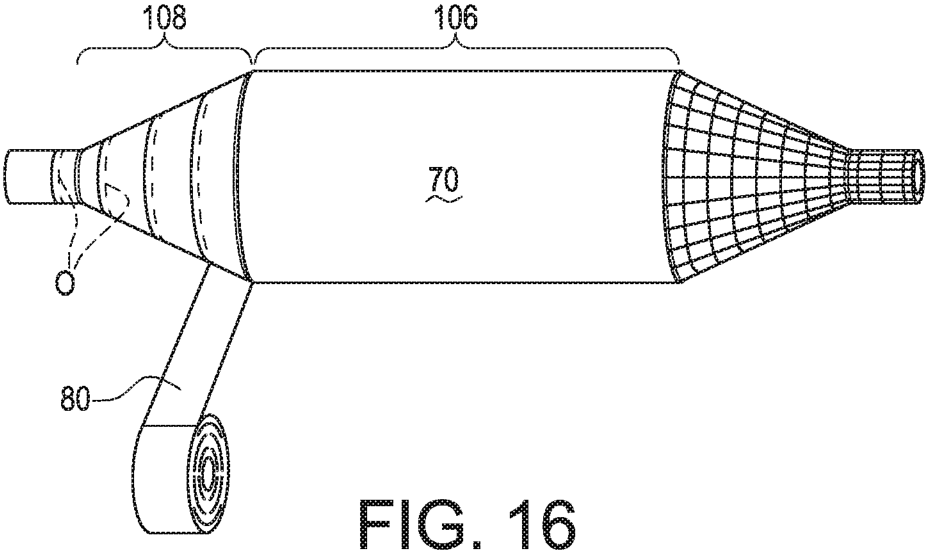

Turning to FIG. 14, a manner of forming the outer layer 16 of the balloon 10 is shown (which may apply to any of the embodiments of balloons described herein). The balloon 10 as illustrated is fiber-reinforced, and thus includes one or more fiber layers, and any mandrel is removed, if present. At least the barrel portion 106 of the as-formed balloon 10 is then provided with an adhesive coating, such as 1-MP, and at least partially deflated. The application of the adhesive coating to the balloon 10 may be done by spraying using a sprayer 150, as shown, but could also be done using other forms of application, such as dip coating, sputtering, brushing, rolling, or the like. While FIGS. 14 to 17 show one or more fiber layers, however, these are purely optional.

A tube 70 is then positioned over the adhesive coating applied to the base layer 100 and any overlying fiber layers 12, 14. The tube 70 may correspond in length 118 to the barrel portion 106 and having an inner diameter 116 may be equal to or greater than the outer diameter of the balloon 10, or may be smaller in diameter and stretched by the base layer 100 on inflation The tube 70 may be fabricated of the same material as the base layer 100 (e.g., a nylon or PET film), and may be formed by extrusion or blow-molding. The tube 70 could also be formed by blow-molding a balloon-shaped structure similar to base layer 100 and cutting off the cone portions 104, 108, which results in a tube in a shape and size similar to barrel portion 106.

The balloon 10 with the adhesive coating and the tube 70 in place over the barrel portion 106 is then inflated. This may be achieved by supplying a pressurized fluid (air) from a source 160 through one neck portion 110 and providing a seal 204 at the open end of the other neck portion 102. With the balloon 10 inflated, a different material is applied to at least one of the cone portions 104, 108 in the same layer as the tube 70 in the barrel portion 106. Specifically, a ribbon of material 80, such as one comprising a polymer film, such as for example pre-stretched PEBAX film. The material 80 may have a thickness similar to that of the tube 70, and may be spirally wrapped or wound around one or both of the cone portions 104, 108, so as to form a spiral wrapping. The width of the material 80 may be relatively narrow, such that two or more passes or winds are required to cover the entirety of each cone portions 104, 108, but the arrangement will ultimately depend on the relative dimensions of the material 80 and the cone portions 104, 108. Adhesive may also be applied to the material 80 during spiral wrapping, but may alternatively or additionally be applied directly to the cone portions 104, 108.

Figure 17:
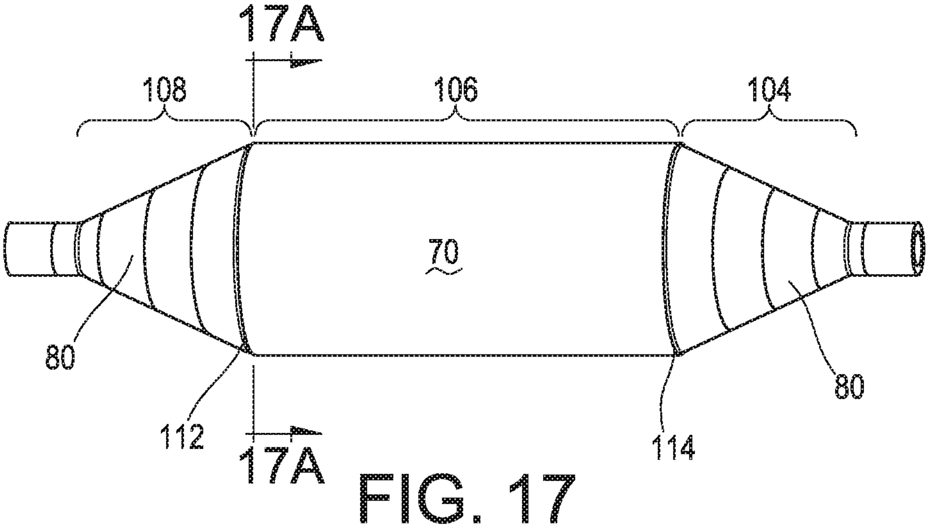
Figure 17A:
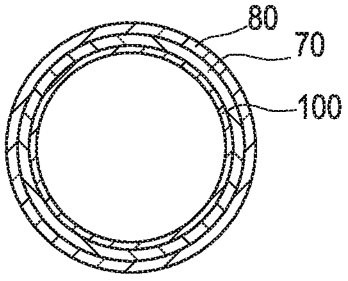

The winding of the material 80 may be done in an overlapping manner. Specifically, each wind or pass of the ribbon of material 80 may at least partially overlap with an adjacent wind (as indicated by phantom lines O indicating overlap). Furthermore, the ribbon of material 80 may overlap with the edges of the tube 70 at the transitions 112, 114 adjacent to the cone portions 104, 108, as can be understood by the cross-sectional view of FIG. 17A. Alternatively, if the ribbon of material 80 is applied first, then the edges of the tube 70 could overlap with it instead. Adhesive may be added between overlapped regions to aid in seamless bonding and transition between regions.

Figure 18:
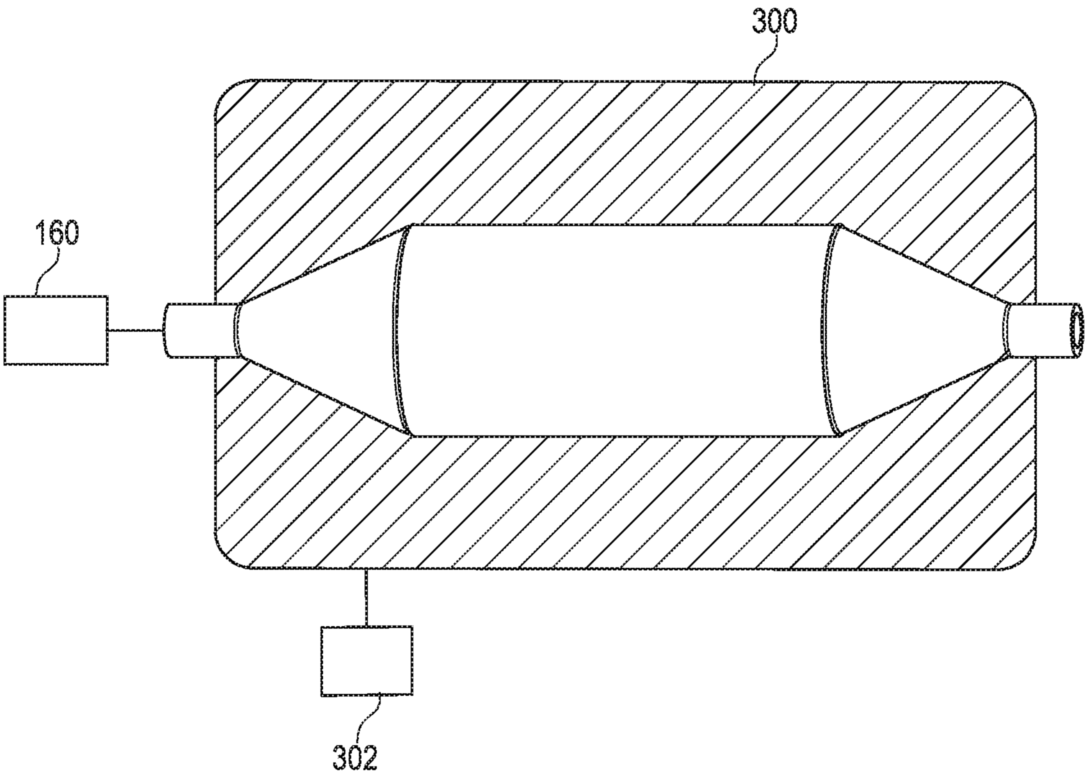

With the tube 70 any spiral wrapping of material 80 in place, the balloon 10 may then be subjected to lamination or consolidation, such as by placing it within a split die 300, as shown in FIG. 18. Heat and pressure may then be applied (note inflation source 202 and heater 203 connected to die 300) to the balloon 10 to activate the previously applied adhesive and allow it to flow along the interface between the tube 70 and material 80 and the underlying base layer 100. Consequently, the tube 70 and the spirally wrapped material 80 becomes fully bonded in place and connected to the underlying layer, such as base layer 100 or any fiber layers 12, 14 present.

Advantageously, this creates a balloon 10 having a hybrid outer layer 16 with several distinct advantages. Specifically, the ability to provide a continuous or seamless tube 70 for the barrel portion 106 allows for the selection of a material with superior properties (e.g. porosity, texture, hardless, etc.) in terms of any associated treatment, such as delivery of a treatment agent or drug (e.g., paclitaxel) coated on the barrel portion, or stent retention/release. The use of a different material for covering the cone portions 104, 108 allows for these regions of the composite balloon 10 to be provided with different properties, such as enhanced flexibility or a differential thickness. Using a spiral wrapping further avoids the need for crimping or folding material around the cone portions 104, 108, which can result in bunching of material when the balloon is laminated and/or folded. This bunched material can also unfurl upon balloon expansion during manufacturing and cause process issues, avoided by using spiral wrapping.

Figure 19:
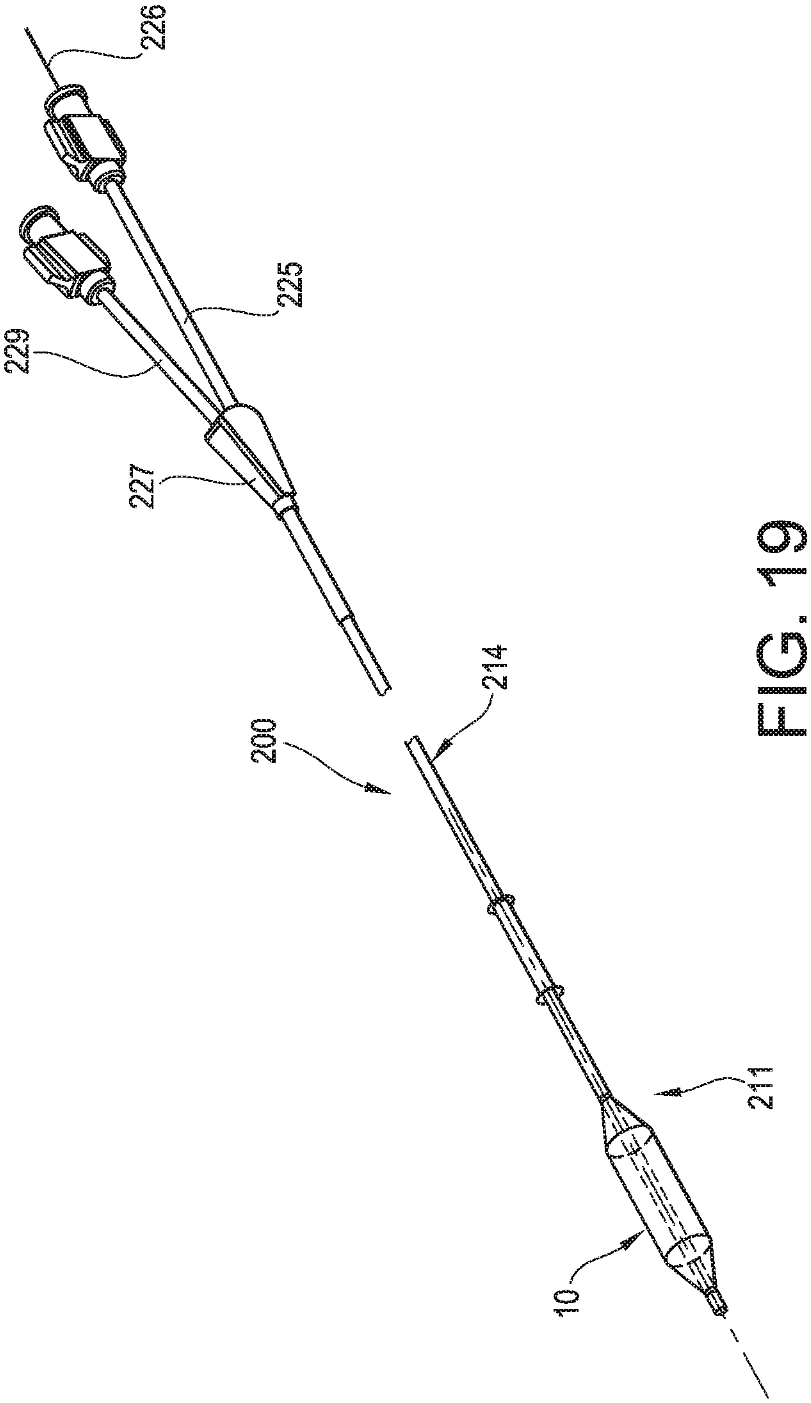
FIGS. 19, 20, 20A, and 21 illustrate a medical balloon with a hybrid outer layer forming part of a catheter.

Turning to FIG. 19, it can be understood that the balloon 10 may form part of a catheter 200 having a shaft 214 with a distal end portion 211 to which the balloon 10 is mounted. The balloon 10 is sealed at balloon ends to allow the inflation via one or more inflation lumens 217 extending within catheter shaft 214 and communicating with the interior of the balloon 10. The catheter 200 may also include a guidewire lumen 223 formed by a shaft 224, which may be within the shaft 214 and, more particularly, within the inflation lumen 217. This lumen 223 directs the guidewire 226 through the catheter 200 (see FIG. 20A), and along the distal end portion of which the balloon 10 may be located, including through a tip 232 distal of balloon 10 distal end.

Figure 20:
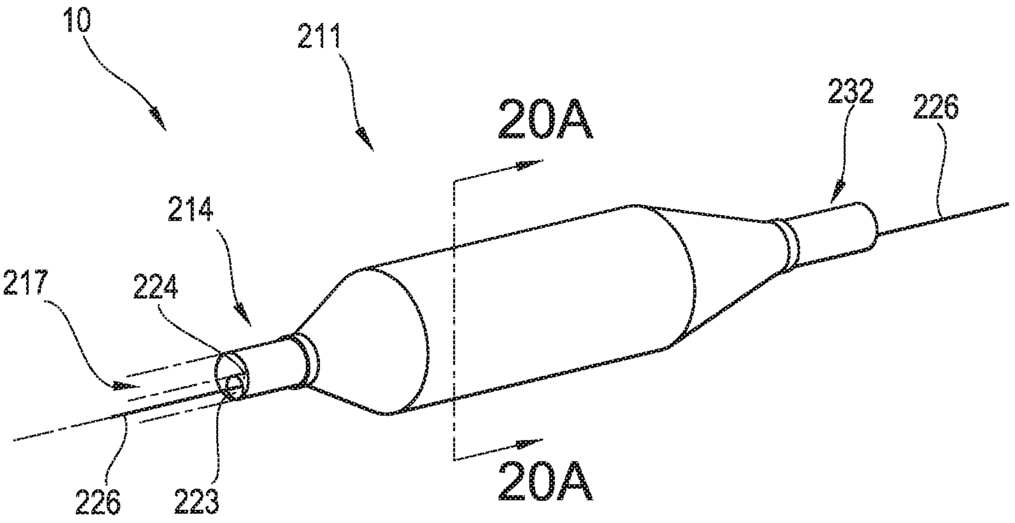
Figure 20A:
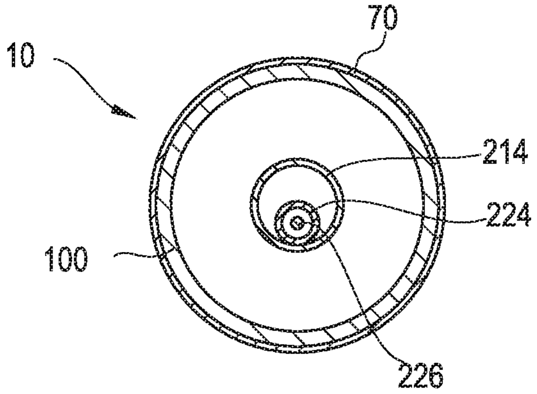
Figure 21:
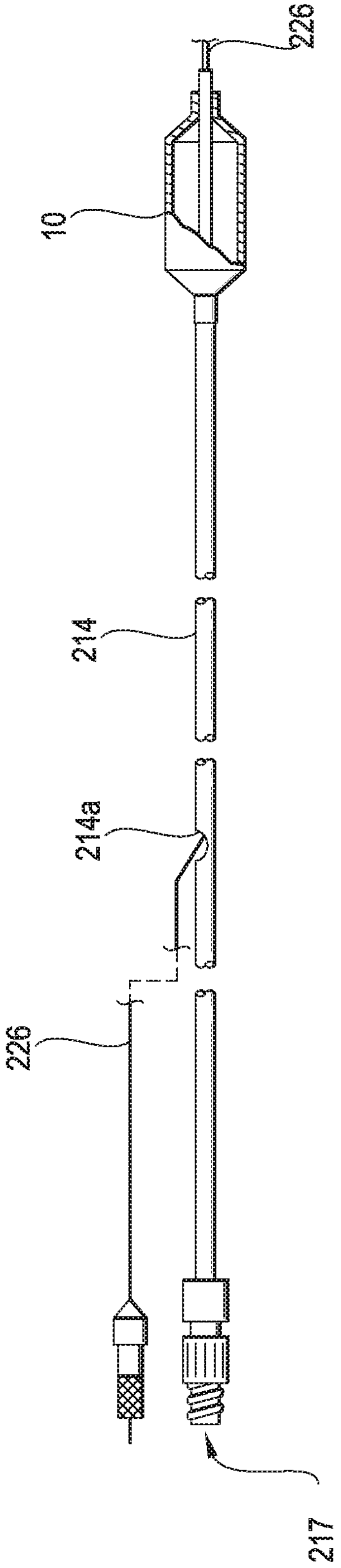

As illustrated in FIG. 20, this guidewire 226 may extend through the proximal end portion of the catheter 200 via a first port 225 of a connector or hub 227 at a proximal end portion 213 of the shaft 214 into the lumen 223 to achieve an "over the wire" (OTW) arrangement, but could also be provided in a "rapid exchange" (RX) configuration (in which the guidewire 226 exits from the shaft 214 at an optional lateral opening 214*a* (see in FIG. 21) closer to the distal end but proximal of balloon 10) or else is fed through the tip 232 at a passage distally of the balloon 10 ("short" RX; not shown). A second port 229 may also be associated with catheter 200, such as by way of connector 227, for introducing a fluid (e.g., saline, a contrast agent, or both) into the interior compartment of the balloon 10 via the inflation lumen 217.

While the embodiments above and shown and described as a balloon having a fiber layer, it should be understood that this is considered an optional feature. Thus, the balloon 10 could simply comprise the base layer 100 and the hybrid outer layer, as proposed, without the inclusion of fibers. Furthermore, any type of intermediate layer may be provided between the base balloon layer 100 and the hybrid outer later to provide the resulting balloon with desired characteristics, such as a particular degree of compliance or an enhanced resistance to bursting.

Summarizing, this disclosure may be considered to relate to the following items:

1. A composite medical balloon, comprising:
   a base balloon layer including first and second tapered portions with a barrel portion therebetween; and
   a hybrid layer comprising a tube for covering the barrel portion and a spiral wrapping for covering at least one of the first and second tapered portions.
2. The composite medical balloon of item 1, wherein the tube comprises an extruded or blow-molded material.
3. The composite medical balloon of item 1 or item 2, wherein the tube comprises a polyamide.
4. The composite medical balloon of any of items 1-3, wherein the base balloon layer comprises a polyamide.
5. The composite medical balloon of any of items 1-4, wherein the spiral wrapping comprises a spirally wound ribbon of material extending from a proximal end of the at least one tapered portion to a distal end of the at least one tapered portion.
6. The composite medical balloon of any of items 1-5, wherein the spiral wrapping overlaps with the tube at a transition from the first or second tapered portion to the barrel portion.
7. The composite medical balloon of any of items 1-6, wherein the spiral wrapping comprises a polyether block amide.
8. The comprise medical balloon of any of items 1-7, further including a spiral wrapping covering the other of the first or second tapered portions.
9. The composite medical balloon of any of items 1-8, wherein the tube is substantially equal in length to a length of the barrel portion of the base balloon layer.
10. The composite medical balloon of any of items 1-9, further including one or more fiber layers between the base balloon layer and the hybrid layer, including for example a longitudinal fiber layer and an angled (hoop) fiber layer, in any order.
11. A composite medical balloon, comprising:
    a balloon including first and second tapered portions having a barrel portion therebetween; and
    a hybrid layer adhesively attached to the balloon, the hybrid layer comprising a tube for covering the barrel portion, a first spirally wrapped ribbon of material for covering the first tapered portion, and a second spirally wrapped ribbon for covering the second tapered portion.
12. The composite medical balloon of item 11, wherein the first spirally wrapped ribbon of material includes a plurality of overlapping winds, including one wind overlapping an edge of the tube or instead being overlapped by an edge of the tube.
13. The composite medical balloon of item 11 or item 12, wherein the tube comprises a polyamide.
14. The composite medical balloon of any of items 11-13, wherein the balloon comprises a polyamide.
15. The composite medical balloon of any of items 11-14, wherein the first and second spirally wrapped ribbons of material comprise a polyether block amide.
16. The composite medical balloon of any of items 11-15, wherein the tube is substantially equal in length to a length of the barrel portion of the balloon.
17. The composite medical balloon of any of items 11-16, further including one or more fiber layers between the balloon and the hybrid layer, including for example a longitudinal fiber layer and an angled (hoop) fiber layer, in any order.
18. A method of forming a composite medical balloon, comprising:
    providing a balloon having a barrel portion between first and second tapered portions;
    forming a hybrid layer on the balloon by applying a tube over the barrel portion of the balloon, and applying a spiral wrapping along one or both of the first and second tapered portion.

19. The method of item 18, further including a step of providing an adhesive to the balloon prior to the forming step.
20. The method of item 19, further including the step of inflating the balloon prior to the step of providing an adhesive, deflating the balloon prior to the step of applying the tube, and re-inflating the balloon prior to the step of applying the spiral wrapping.
21. The method of any of items 18-20, wherein the step of applying the spiral wrapping comprises applying a spirally wrapped ribbon of material to each of the first and second tapered portions of the balloon.
22. The method of any of items 18-21, further including the step of laminating the balloon, the tube, and the spiral wrapping.
23. The method of any of items 18-22, further including the step of applying one or more fiber layers to the balloon, including for example a longitudinal fiber layer and an angled (hoop) fiber layer, in any order.

As used herein, the following terms have the following meanings:

"A", "an", and "the" as used herein refers to both singular and plural referents unless the context clearly dictates otherwise. By way of example, "a compartment" refers to one or more than one compartment.

"About," "substantially," or "approximately," as used herein referring to a measurable value, such as a parameter, an amount, a temporal duration, and the like, is meant to encompass variations of +/−20% or less, including +/−10% or less, +/−5% or less, +/−1% or less, and +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Although the invention has been described in conjunction with specific embodiments, many alternatives, modifications, and variations will be apparent to those skilled in the art. Accordingly, it embraces all such alternatives, modifications, and variations that fall within the appended claims' spirit and scope. All publications, patents and patent applications mentioned in this specification are herein incorporated in their entirety by reference into the specification, to the same extent as if each individual publication, patent or patent application was specifically and individually indicated to be incorporated herein by reference. In addition, or identification of any reference in this application shall not be construed as an admission that such reference is available as prior art to the present disclosure.

The invention claimed is:

1. A composite medical balloon, comprising:
a base balloon layer including first and second tapered portions and a barrel portion therebetween, the base balloon defining a first balloon length extending from a longitudinal location within the first tapered portion to a longitudinal location within the second tapered portion; and
a hybrid layer over the base balloon layer, the hybrid layer comprising a seamless tube covering the barrel portion and a spiral wrapping covering at least one of the first and second tapered portions;
wherein neither the seamless tube nor the spiral wrapping extends an entire length of the first balloon length.

2. The composite medical balloon of claim 1, wherein the tube comprises an extruded or blow-molded material.

3. The composite medical balloon of claim 1, wherein the tube comprises a polyamide.

4. The composite medical balloon of claim 3, wherein the base balloon layer comprises a polyamide.

5. The composite medical balloon of claim 1, wherein the spiral wrapping comprises a spirally wound ribbon of material extending from one end of the first or second tapered portion to another end of the corresponding tapered portion.

6. The composite medical balloon of claim 1, wherein the spiral wrapping overlaps with the tube at a transition from the first or second tapered portion to the barrel portion.

7. The composite medical balloon of claim 1, wherein the spiral wrapping comprises a polyether block amide.

8. The comprise medical balloon of claim 1, further including a spiral wrapping covering the other of the first or second tapered portions.

9. The composite medical balloon of claim 8, wherein the tube is substantially equal in length to a length of the barrel portion of the base balloon layer.

10. The composite medical balloon of claim 1, further including one or more fiber layers between the base balloon layer and the hybrid layer.

11. A composite medical balloon, comprising:
a balloon including first and second tapered portions having a barrel portion therebetween, the balloon defining a balloon length extending from a first longitudinal location at a proximal end of the first tapered portion to a second longitudinal location at a distal end of the second tapered portion; and
a hybrid layer adhesively attached to the balloon, the hybrid layer comprising a tube made of a first material covering the barrel portion, a first spirally wrapped ribbon made of a second material covering the first tapered portion, and a second spirally wrapped ribbon made of the second material for covering the second tapered portion;
wherein the first material is different from the second material; and
wherein none of the tube, the first spiral wrapped ribbon, and the second spiral wrapped ribbon extends along an entire length of the balloon length.

12. The composite medical balloon of claim 11, wherein the first spirally wrapped ribbon of material includes a plurality of overlapping winds, including one wind overlapping an edge of the tube.

13. The composite medical balloon of claim 11, wherein the tube comprises a polyamide.

14. The composite medical balloon of claim 13, wherein the balloon comprises a polyamide.

15. The composite medical balloon of claim 11, wherein the first or second spirally wrapped ribbons of material comprise a polyether block amide.

16. The composite medical balloon of claim 11, wherein the tube is substantially equal in length to a length of the barrel portion of the balloon.

17. The composite medical balloon of claim 11, further including a fiber layer between the balloon and the hybrid layer.

18. The composite medical balloon of claim 11, wherein the first material imparts a first property to the tube;

wherein the second material imparts a second property to the first tapered portion and the second tapered portion; and wherein the first property is different from the second property.

* * * * *